US005395759A

United States Patent [19]

Holmes et al.

[11] Patent Number: 5,395,759

[45] Date of Patent: Mar. 7, 1995

[54] DNA SEQUENCE AND AMINO ACID SEQUENCE ENCODING THE HUMAN ROTAVIRUS MAJOR OUTER CAPSID GLYCOPROTEIN

[75] Inventors: Ian H. Holmes, Canterbury; Michael L. Dyall-Smith, Kew, both of Australia

[73] Assignee: The University of Melbourne, Victoria, Australia

[21] Appl. No.: 474,642

[22] PCT Filed: Apr. 29, 1985

[86] PCT No.: PCT/AU85/00096

§ 371 Date: Feb. 4, 1987

§ 102(e) Date: Feb. 4, 1987

[87] PCT Pub. No.: WO85/05122

PCT Pub. Date: Nov. 21, 1985

Related U.S. Application Data

[63] Continuation of Ser. No. 824,704, Feb. 4, 1987, abandoned.

[30] Foreign Application Priority Data

Apr. 27, 1984 [AU] Australia .............................. PG4733

[51] Int. Cl.[6] ........................ C12N 5/00; C12N 15/00; C07K 13/00; C07H 17/00

[52] U.S. Cl. .............................. 435/240.1; 435/320.1; 530/395; 536/23.72

[58] Field of Search .......................... 536/27; 530/350; 424/89; 435/69.1, 69.3, 172.3, 252.3

[56] References Cited

PUBLICATIONS

Green, Kim Y. et al., (1987) "Comparison of the Amino Acid Sequences of the Major Neutralization Protein of Four Human Rotavirus Serotypes", *Virology* 161, 153–159.

Both et al. (1983) Serotype Specific Glycoprotein of Simian 11 Rotavirus: Coding Assignment and Gene Sequence, PNAS 80, 3091–3095.

Estes et al. (1989) "Rotavirus Gene Structure and Function" *Micro-Biological Reviews* 53, 410–449.

Thouless, M. E., et al. (1977) Serological relationships between rotaviruses from different species as studies by complement fixation and neutralization. *Arch. Virol.* 53: 287–294.

Dyall-Smith, M. L., et al. (1981) Gene-coding assignments of rotavirus double-stranded RNA segments 10 and 11. *J. Virol.* 38: 1099–1103.

Kalica, A. R., et al., (1981) Genes of human (strain Wa) and bovine (strain UK) rotaviruses that code for neutralization and subgroup antigens. *Virology* 112: 385–390.

Wyatt, R. G., et al. (1982) Definition of human rotavirus serotypes by plaque reduction assay. Infect. Immun. 37:110–115.

Sonza, S., et al., (1983) Derivation of neutralizing monoclonal antibodies against rotavirus. *J. Virol.* 45:1143–1146.

Dyall-Smith, M. L., et al. (1983) Gene mapping of rotavirus double-stranded RNA segments by northern blot hybridization: Application to segments 7, 8, and 9. *J. Virol.* 46:317–320.

Dyall-Smith, M. L., et al., (1983) Cloning and sequencing of UK bovine rotavirus gene segment 7: marked sequence homology with simian rotavirus gene segment 8. *Nucelic Acids Res.* 11:3351–3362.

Elleman, T. C., et al., (1983) Nucleotide sequence of the gene encoding the serotype-specific glycoprotein of UK bovine rotavirus *Nucleic Acids Res.* 11: 4689–4701.

*Primary Examiner*—Elizabeth C. Weimar
*Assistant Examiner*—Deborah Crouch
*Attorney, Agent, or Firm*—Scully, Scott, Murphy & Presser

[57] ABSTRACT

A material being a dsRNA gene segment coding for the major outer capsid glycoprotein of a rotavirus.

4 Claims, 7 Drawing Sheets

Hu/5 Segment 8

5'-GGCTTTAAAAACGAGAATTTCCGTCTGGCTAGCGGTTAGCTCTTTTTA48

ATG TAT GGT ATT GAA TAT ACC ACA ATT CTG ACC ATT TTG87
Met Tyr Gly Ile Glu Tyr Thr Thr Ile Leu Thr Ile Leu13
ATA TCT ATC ATA TTA TTG AAT TAT ATA TTA AAA ACT123
Ile Ser Ile Ile Leu Leu Asn Tyr Ile Leu Lys Thr25

ATA ACT AAT ACG ATG GAC TAC ATA ATT TTC AGG TTT TTA162
Ile Thr Asn Thr Met Asp Tyr Ile Ile Phe Arg Phe Leu38
CTA CTC ATT GCT TTA ATA TCA CCA TTT GTA AGG ACA198
Leu Leu Ile Ala Leu Ile Ser Pro Phe Val Arg Thr50

CAA AAT TAT GGC ATG TAT TTA CCA ATA ACG GGA TCA CTA237
Gln Asn Tyr Gly Met Tyr Leu Pro Ile Thr Gly Ser Leu63
GAC GCT GTA TAT ACG AAT TCT ACT AGT GGA GAG CCA273
Asp Ala Val Tyr Thr Asn Ser Thr Ser Gly Glu Pro75

TTT TTA ACT TCG ACG CTG TGT TTA TAC TAT CCA GCA GAA312
Phe Leu Thr Ser Thr Leu Cys Leu Tyr Tyr Pro Ala Glu88
GCT AAA AAT GAG ATT TCA GAT GAT GAA TGG GAA AAT348
Ala Lys Asn Glu Ile Ser Asp Asp Glu Trp Glu Asn100

FIG. 4.

ACT TTA TCA CAA TTA TTT TTA ACT AAA GGA TGG CCA ATT$^{387}$
Thr Leu Ser Gln Leu Phe Leu Thr Lys Gly Trp Pro Ile$_{113}$
GGA TCA GTT TAT TTT AAA GAC TAC AAT GAT ATT AAT$^{423}$
Gly Ser Val Tyr Phe Lys Asp Tyr Asn Asp Ile Asn$_{125}$

ACA TTT TCT GTG AAT CCA CAA CTA TAT TGT GAT TAT AAT$^{462}$
Thr Phe Ser Val Asn Pro Gln Leu Tyr Cys Asp Tyr Asn$_{138}$
GTA GTA TTG ATG AGA TAT GAC AAT ACA TCT GAA TTA$^{498}$
Val Val Leu Met Arg Tyr Asp Asn Thr Ser Glu Leu$_{150}$

GAT GCA TCA GAG TTA GCA GAT CTT ATA TTG AAT GAA TGG$^{537}$
Asp Ala Ser Glu Leu Ala Asp Leu Ile Leu Asn Glu Trp$_{162}$
CTG TGC AAT CCT ATG GAT ATA TCG CTT TAC TAT TAT$^{573}$
Leu Cys Asn Pro Met Asp Ile Ser Leu Tyr Tyr Tyr$_{175}$

CAA CAA AGT AGC GAA TCA AAT AAA TGG ATA TCG ATG GGA$^{612}$
Gln Gln Ser Ser Glu Ser Asn Lys Trp Ile Ser Met Gly$_{188}$
ACA GAC TGC ACG GTA AAA GTT TGT CCA CTC AAT ACA$^{648}$
Thr Asp Cys Thr Val Lys Val Cys Pro Leu Asn Thr$_{200}$

CAA ACC CTA GGG ATT GGA TGC AAA ACT ACG GAT GTA AAC$^{687}$
Gln Thr Leu Gly Ile Gly Cys Lys Thr Thr Asp Val Asn$_{213}$
ACA TTT GAG ATT GTT GCG TCG TCT GAA AAA TTA GTA$^{723}$
Thr Phe Glu Ile Val Ala Ser Ser Glu Lys Leu Val$_{225}$

FIG. 4a.

ATT ACT GAC GTT GTA AAT GGT GTT AAC CAT AAC ATA AAT 762
Ile Thr Asp Val Val Asn Gly Val Asn His Asn Ile Asn 238
ATT TCA ATA AAT ACG TGC ACT ATA CGC AAC TGT AAT 798
Ile Ser Ile Asn Thr Cys Thr Ile Arg Asn Cys Asn 250

AAA TTA GGA CCA CGA GAA AAT GTT GCT ATA ATT CAA GTT 837
Lys Leu Gly Pro Arg Glu Asn Val Ala Ile Ile Gln Val 263
GGT GGA CCG AAC GCA TTA GAT ATC ACT GCT GAT CCA 873
Gly Gly Pro Asn Ala Leu Asp Ile Thr Ala Asp Pro 275

ACA ACA GTC CCA CAA GTT CAA AGA ATC ATG CGA ATA AAT 912
Thr Thr Val Pro Gln Val Gln Arg Ile Met Arg Ile Asn 288
TGG AAA AAA TGG TGG CAA GTA TTT TAT ACA GTA GTT 948
Trp Lys Lys Trp Trp Gln Val Phe Tyr Thr Val Val 300

GAC TAT ATT AAC CAA GTT ATA CAA GTC ATG TCC AAA CGA 987
Asp Tyr Ile Asn Gln Val Ile Gln Val Met Ser Lys Arg 313
TCA AGA TCA TTA GAC GCA GCT GCT TTT TAT TAT AGA 1023
Ser Arg Ser Leu Asp Ala Ala Ala Phe Tyr Tyr Arg 325

ATT TAG ATATAGATTTGGTCAGATTTGTATGATGTGACC-3' 1062
Ile 326

FIG. 4B

Series A

| | | |
|---|---|---|
| (i) | Hu/5 | C L Y Y P A E A K N E I S D D E W E N T L S |
| (ii) | SA11 | C L Y Y P T E A A T E I N D N S W K D T L S |
| (iii) | UK | C L Y Y P V E A S N E I A D T E W K D T L S |

Series B

| | | |
|---|---|---|
| (i) | Hu/5 | Y D N T S E L D A S E L |
| (ii) | SA11 | Y D A T L Q L D M S E L |
| (iii) | UK | Y D S T Q E L D M S E L |

Series C

| | | |
|---|---|---|
| (i) | Hu/5 | G I G C K T T D V N T F E I V A S S E K L |
| (ii) | SA11 | G I G C L T T D A T T F E E V A T A E K L |
| (iii) | UK | G I G C L I T N P D T F E T V A T T E K L |

FIG. 5

DNA SEQUENCE AND AMINO ACID SEQUENCE ENCODING THE HUMAN ROTAVIRUS MAJOR OUTER CAPSID GLYCOPROTEIN

This application is a continuation of application Ser. No. 824,704, filed Feb. 4, 1987.

This invention relates to rotavirus, genes, gene segments, cloned genes and segments and products obtained therefrom including diagnostic reagents and vaccines.

Rotavirus is now recognized by the World Health Organization as a major cause of infantile gastroenteritis, and a high priority has been placed on control of this disease by the production of a suitable vaccine (1). Cross-neutralization tests indicate four (or possibly five) (2–4) serotypes of human rotavirus and animal studies appear to show little cross-protection between serotypes (5). Thus a potential vaccine may have to incorporate all the known human serotypes. The virus serotype has recently been shown to be determined by the major outer shell glycoprotein (6–10) (a virus surface protein), and the gene segments coding for this protein from a bovine (UK) and a simian (SA11) rotavirus have recently been sequenced (11, 12). To date however, no such gene from human rotavirus has been analysed. We therefor cloned and sequenced the gene encoding this protein from a human rotavirus. Hu/5 (isolated in Melbourne, Australia) belonging to serotype 2.

The present invention provides a human rotavirus gene and a cloned human rotavirus gene, the use of such genes to obtain expression of antigenic viral proteins such as in bacterial/procaryotic or eucaryotic expression systems and the expression products obtained and further including vaccines and diagnostic reagents obtained therefrom.

The present invention also provides the dsRNA gene segment coding for the major outer capsid glycoprotein of a human rotavirus and, without prejudice to the generality of the foregoing, that human rotavirus may be Hu/Australia/5/77 (serotype 2), a DNA copy of same, a clone thereof, or a vector or a host cell containing same, peptide sequences obtained therefrom. Of particular interest are vectors such as plasmids obtained therefrom and host cell containing same.

The present invention also provides a material comprising a nucleotide sequence coding for at least part of the major outer capsid glycoprotein of a rotavirus.

In one instance the present invention provides at least one of the nucleotide sequences from nucleotide numbers 291–357, 480–513 and 657–720 of a rotavirus major outer capsid glycoprotein gene.

In another instance the present invention provides at least one of the amino acid sequences from amino acid numbers 82–103, 144–155 and 204–224 for which the nucleotide sequences of a rotavirus major outer capsid glycoprotein gene code.

In a particularly preferred instance the present invention provides a material comprising a nucleotide sequence encoding, or an amino acid sequence being, a. an amino acid sequence of 22 amino acids commencing CLYYP and terminating TLS, b. an amino acid sequence of 12 amino acids commencing YD and terminating SEL, or c. an amino acid sequence of 21 amino acids commencing GIGC and terminating EKL, and derived from a nucleotide sequence coding for a major outer capsid glycoprotein of a rotavirus.

Specific portions of cloned genes are provided by this invention and the invention extends to products obtained therefrom including anti-sera or anti-bodies prepared by utilization of such amino acid sequences.

This invention will be exemplified by the following description.

MATERIALS AND METHODS

Virus growth and purification

The human rotavirus Hu/5 (Hu/Australia/5/77) (13) was grown in MA104 cells and purified as described previously (14).

Cloning rotavirus cDNA

The procedure for producing cDNA from rotavirus dsRNA, and cloning it into the PstI site of the plasmid pBR322 has been described previously by Dyall-Smith et al. (15).

Identification of cloned copies of the major outer shell glycoprotein gene of Hu/5 rotavirus Since the UK bovine rotavirus gene encoding the major outer shell glycoprotein (gene 8 of this virus) had previously been cloned (11), this was used to screen the Hu/5 clones. To eliminte pBR322 sequences, the UK gene 8 clone was digested with PstI and the insert separated by agarose gel electrophoresis. The insert was then $^{32}$p-labelled by nick translation (16) and hybridized to transformant bacterial colonies which had been lysed on nitrocellulose filters (17).

Northern blot analyses

Hu/5 dsRNA was separated on a polyacrylamide gel and immobilized on aminophenylthioether (APT) paper as described previously (7), except that the RNA was loaded right along the tope of the stacking gel (which was not divided into wells). After transfer, the blot was cut (lengthwise) into strips and hybridized to $^{32}$p-labelled cDNA or nick translated DNA probes. Labelled cDNA was prepared from Hu/5 segments 7, 8 and 9 dsRNA (isolated by agarose gel electrophoresis) using reverse transcriptase (Life Sciences Inc. U.S.A.) and random primer DNA (prepared from calf thymus DNA) (18). Hybridization conditions were as follows: blots were prehybridized for 15 min at 60° C. in 5×Denhardt's solution containing 10 mM HEPES (pH 7.0), 0.1% SDS, 3×SSC, 10 mug/ml *E. coli* tRNA, and 18 mug/ml herring sperm DNA, and then hybridized (18 hr, 65° C.) to the appropriate DNA probe. Blots were washed twice for 15 min at 60° C. in 0.2×SSC containing 0.1% SDS, and exposed to x-ray film.

DNA sequencing

The pBR322 clone was digested with PstI, and the insert subcloned into the PstI site of M13 mp8 (19). Sequences were determined from the M13 ssDNA template by the chain termination method (20) using exonuclease III-treated restriction fragments (except the EcoRI/TaqI fragment) as primers (21). A synthetic primer (5'-dGGTCACAT-3'), complementary to the 3' end of the mRNA-sense strand was also used.

Electrophoresis of rotavirus dsRNA dsRNA was extracted from purified virus preparations using a simplified version of the method of Herring et al. (22). Briefly, 5 mul of a purified virus suspension was added to 200 mul of 0.1M sodium acetate buffer (pH5.0) containing 1% sodium dodecyl. sulphate (SDS) and vortexed for 1 min with an equal volume of 'phenol'/chloroform mixture. The phases were separated by a brief centrifugation (2', 10,000 g) and an aliquot of the aqueous phase (5–20 mul) mixed with 20 mul of sample buffer (25% (v/v) glycerol, 0.2% bromphenol blue, 0.4M Tris-Cl (pH6.8)) and analysed on a 10% polyacrylamide gel (0.75 mm thick) using the buffer system of Laemmli (23) (but without SDS). The gel was silver stained according to the method of Herring et al. (22), except that the incubation in silver nitrate was for 30 min instead of 2 hr, and sodium borohydride was omitted from the developing solution. Degassing of solutions was also found to be unnecessary.

DESCRIPTION OF THE DRAWINGS

Reference will be made to the accompanying drawings in which:

FIGS. 4 4*a* and 4*b* are a Nucleotide sequence and predicted amino-acid sequence of the mRNA-sense DNA strand of the segment 8 clone of Hu/5 rotavirus. In phase termination codons are indicated by solid bars.

FIG. 5 is a comparison of the predicted amino-acid sequence of portion of the major outer shell glycoproteins of Hu/5 as compared to the equivalent regions of SA11 and UK rotavirus.

DETAILED DESCRIPTION OF THE INVENTION

Figure 1:
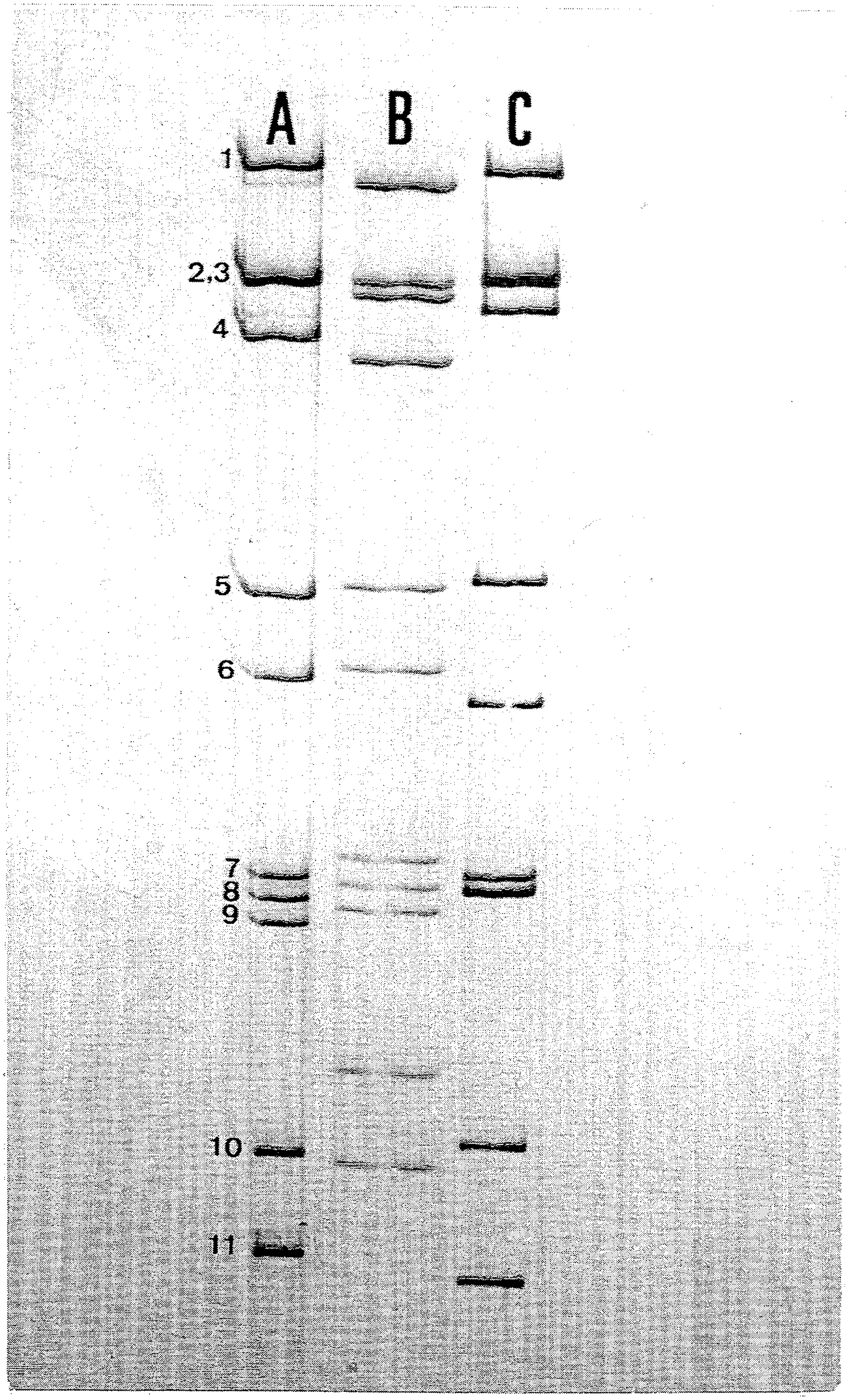
FIG. 1 is polyacrylamide gel electrophoresis of rotavirus dsRNA extracted from A, Wa; B, Hu/5; and C, UK viruses. The eleven gene segments of Wa virus have been numbered from largest to smallest.

The rotavirus genome consists of eleven dsRNA segments which upon gel electrophoresis form a characteristic pattern of bands; the virus electropherotype (24). The gel patterns of genomic RNA from the human rotavirus Hu/5 (Hu/Australia/5/77) (13), Wa (25) (human, serotype 1) and UK (26) viruses are shown in FIG. 1, and demonstrate clearly that Hu/5 has a "short" pattern (due to the positions of segments 10 and 11) (27, 14) compared to the "long" gel patterns of the other two. The "short" pattern has previously been associated with serotype 2 human rotaviruses (27–29), and when the Hu/5 virus was serotyped in this laboratory according to the method of Thouless et al. (30) (using typing antisera kindly supplied by M. Thouless and Wa, S2 (31) and SA11 (32) viruses as serotype 1, 2 and 3 reference strains) (4, 33) it was indeed found to belong to serotype 2 (data not shown).

Figure 2:
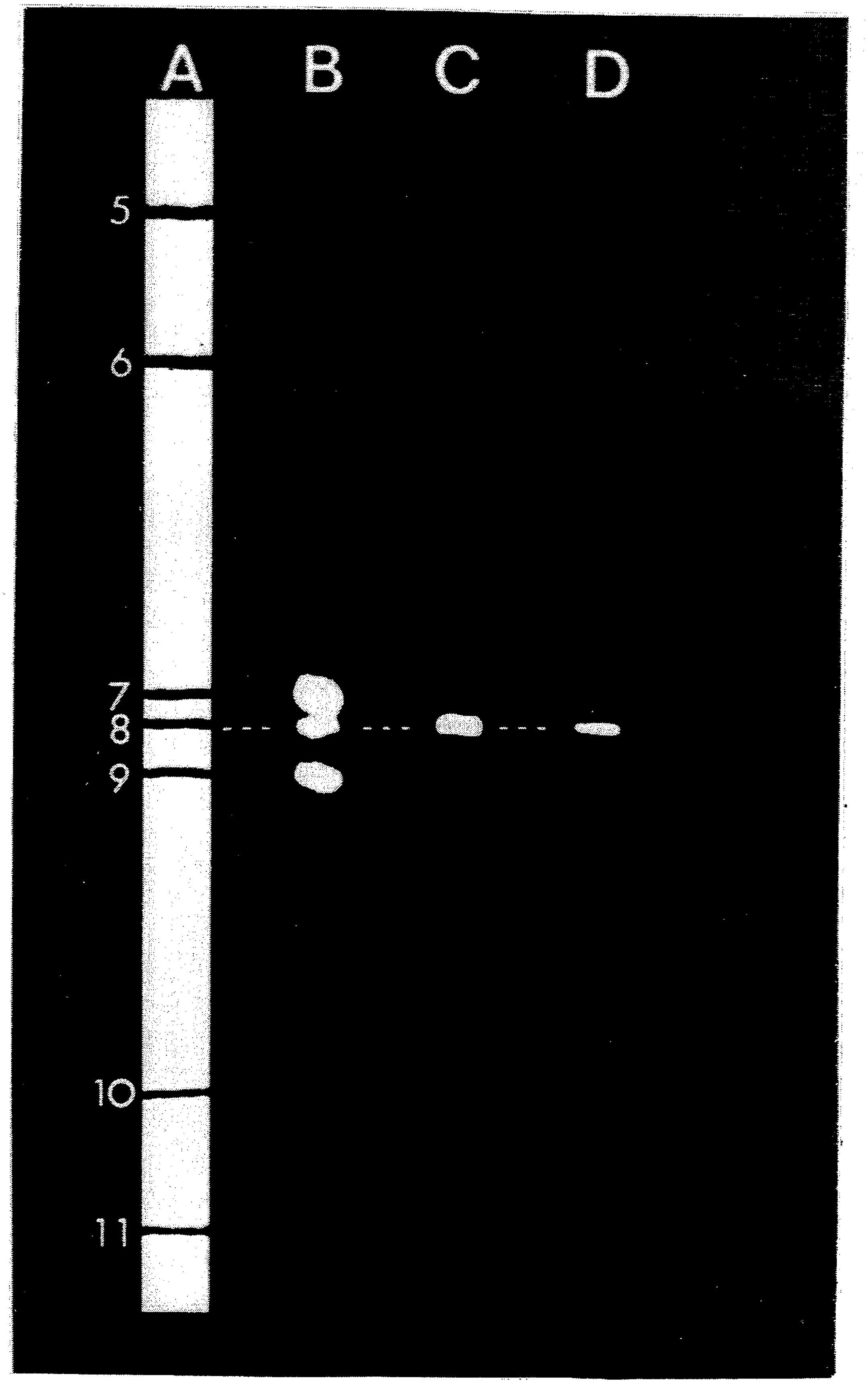
FIG. 2 is northern blot hybridizations identifying gene segment 8 of Hu/5 rotavirus as encoding the major outer shell glycoprotein. Track A shows part of the ethidium bromide-stained polyacrylamide gel of Hu/5 dsRNA (only segments 5–11 shown). The RNA bands were transferred to APT-paper and the paper cut into strips (lengthwise). The blots were hybridized to $^{32}$p-labelled DNA probes prepared from; B, RNA segments 7, 8 and 9 of Hu/5 virus (to precisely locate these bands); C, a pBR322 clone of UK virus segment 8 (the gene encoding the major outer shell glycoprotein of this virus), and D, a pBR322 clone of the glycoprotein gene of Hu/5 virus.
Figure 3:
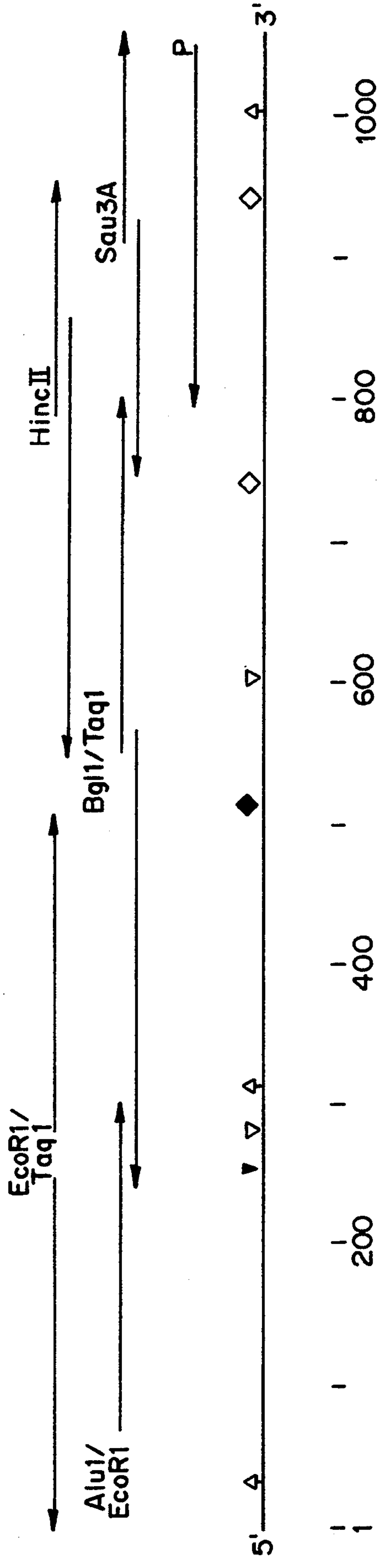
FIG. 3 is a summary of the sequencing strategy used to determine the nucleotide sequence of the cloned DNA copy of dsRNA gene segment 8 of Hu/5 rotavirus. The number of nucleotides are indicated below the line representing the clone, and the restriction sites used to generate sequencing primers are shown immediately above ( , AluI; ,Eco RI; , TaqI; , BglII; , HincII) A synthetic primer (5'-dGGTCACAT-3'), complementary to the 3' end of the mRNA-sense strand was also used (primer P). The orientation of the clone is such that the mRNA-sense DNA strand is in the indicated 5' to 3' direction.

Hu/5 genomic dsRNA was converted into DNA and cloned into the PstI site of pBR322 as described previously for UK rotavirus (15). Clones of the major outer shell glycoprotein were identified using a probe ($^{32}$p-labelled by nick translation) prepared from a cloned glycoprotein gene from UK bovine rotavirus (11). The identity of one of these clones was confirmed by Northern blot analyses which also mapped this gene to segment 8 of Hu/5 rotavirus (FIG. 2). This clone was sequenced according to the strategy shown in FIG. 3 and the full, sequence is shown in FIG. 4. The clone is a full-length copy of the glycoprotein gene since a) it is the same length (i.e. 1062 bp) as the corresponding UK and SA11 genes, and b) it has the characteristic conserved 5' and 3' terminal sequences (34, 35). It has one open reading frame (the other frames contain multiple stop codons) capable of coding for a protein of 326 amino acids, and 5' and 3' non-coding regions of 48 and 36 bp respectively. In these respects it is identical to UK and SA11 glycoprotein genes (11, 12). The base sequence homologies of the Hu/5, SA11 and UK glycoprotein genes are as follows: Hu/5:UK or SA11=74% and UK:SA11=77.6%. They are obviously closely related.

When the predicted amino-acid sequence of the Hu/5 virus glycoprotein gene was compared to those of UK and SA11 (FIG. 5) an even greater degree of similarity was observed. In pair-wise comparison the amino-acid sequence homologies are; Hu/5:UK:=75.8%, Hu/5-:SA11:=75.2% and UK:SA11=85.6%. Studies with UK and SA11 viruses have shown that the glycosylation of these proteins is asparagine-linked and consists of simple ("high mannose") oligosaccharide moieties (36–38). Studies show that all three proteins retain potential glycosylation site (of the type Asn-X-$_{Thr}{}^{Ser}$) at residue 69, which for SA11 is the only such site. The Hu/5 and UK proteins also have potential sites at residues 238 (both), 146 (Hu/5) and 318 (UK), however the distribution of carbohydrate in these proteins is not known.

All glycoproteins of eukaryotic cells require a signal sequence for vectorial transport across the endoplasmic reticulum (39). Using the general rules proposed by Perlman and Halvorson (40) a typical signal sequence can be discerned in the first 25 residues of the 3 rotavirus glycoproteins. Their putative hydrophobic core sequences (res. 6–19) are preceded by the charged residue Glu- (res. 5). The likely cleavage sites are after serine at position 15, or after position 25 (Ser/Thr). Recent studies with SA11 virus (41) have demonstrated a cleaved signal sequence for this protein with a molecular weight (1,500 MW) consistent with the earlier predicted cleavage site. It is interesting that the first 25 residues of all three glycoproteins show relatively greater conservation than the subsequent 25.

While the glycoproteins of Hu/5, UK and SA11 are very similar in amino-acid sequence, they must differ in antigenically significant regions since the three viruses are serotypically different, i.e. Hu/5 is a human serotype 2 virus, UK belongs to a bovine serotype (33), and SA11 although of simian origin is serologically human type 3 (33). Results of competition experiments using monoclonal antibodies to SA11 virus have demonstrated only one or possibly two epitopes involved in neutralization (42).

To locate the major antigenic regions of the glycoprotein we have used monoclonal antibodies which neutralize SA11 rotavirus. By selecting mutants resistant to neutralization and sequencing their glycoprotein genes we were able to identify three (A, B and C) important regions (M. L. Dyall-Smith, I. Lazdins, G. W. Tregear and I. H. Holmes, manuscript in preparation for publication). These are amino acids 82–103[(A)], 144–155[(B)] and 204–224[(C)], at which region C appears to be the most important. A mutation in the C region at amino acid 211 caused a ten fold decrease in the ability of polyclonal antiviral anti serum to neutralize virus, indicating that this is a site of major antigenic importance.

The sequence data (above) support the wealth of serological evidence (43–45) that rotaviruses are a closely related group. Indeed they appear to be much more closely related than the three serotypes of mammalian reovirus, which are structurally and epidemiologically similar to rotaviruses (46). The genes encoding the serotype-specific protein of the three reovirus serotypes are related only to the extent of 1–12% (47). The fact that two simian rotaviruses, SA11 and rhesus (MM18006) are serologically closely related (33) yet were isolated over 20 years apart (48, 49) also suggests that rotavirus serotypes are fairly stable antigenically, unlike influenza A subtypes which show antigenic drift (50). While many more rotavirus glycoprotein genes need to be studied, the limited number of human serotypes so far detected and the apparently low level of antigenic drift look encouraging for the development of human rotavirus vaccines.

Concerning vaccine preparation, in general it will be best if the rotavirus genetic material of this invention is introduced into a bacterium and this may be effected in accordance with the procedures of Formal et al (51), Silhavy et al (52) or Roberts et al (53).

REFERENCES

1. Bull. W.H.O. (1983) 61, 251–254.
2. Sato, K., Inaba, Y., Miura, Y., Tokuhisa, S. and Matumoto, M. (1982). Arch. Virol. 73, 45–50.
3. Thouless, M. E., Beards, M. and Flewett, T. H. (1982). Arch. Virol. 73, 219–230.
4. Wyatt, R. G., James, H. D., Pittman, A. L., Hoshino, Y., Greenberg, H. B., Kalica, A. R., Flores, J. and Kapikian, A. Z. (1983). J. Clin. Micro. 18, 310–317.
5. Gaul, S. K., Simpson, T. F., Woode, G. N. and Fulton, R. W. (1982). J. Clin. Micro. 16, 495–503.
6. Kalica, A. R., Greenberg, H. B., Wyatt, R. G., Flores, J., Sereno, M. M., Kapikian, A. Z. and Chanock, R. M. (1981). Virology 112, 385–390.
7. Dyall-Smith, M. L., Azad, A. A. and Holmes, I. H. (1983). J. Virol. 46, 317–320.
8. Kantharidis, P., Dyall-Smith, M. L. and Holmes, I. H. (1983). J. Virol. 48, 330–334.
9. Bastardo, J. W. McKimm-Breschkin, J. L., Sonza, S., Mercer, L. D. and Holmes, I. H. (1981). Infect. Immun. 34, 641–647.
10. Sonza, S., Breschkin, A. M. and Holmes I. H. (1983). J. Virol. 45, 1143–1146.
11. Elleman, T. C., Hoyne, P. A., Dyall-Smith, M. L., Holmes, I. H. and Azad, A. A. (1983). Nucleic Acids Res. 11, 4689–4701.
12. Both, G. W., Mattick, J. S. and Bellamy, A. R. (1983). Proc. Natl. Acad. Sci. U.S.A. 80, 3091–3095.
13. Albert, M. J. and Bishop, R. F. (1984). J. Med. Virol. In press.
14. Dyall-Smith, M. L. and Holmes, I. H. (1981). J. Virol. 38, 1099–1103.
15. Dyall-Smith, M. L., Elleman, T. C., Hoyne, P. A., Holmes, I. H. and Azad, A. A. (1983). Nucleic Acids Res. 11, 3351–3362.
16. Rigby, P. W. S., Dieckman, M., Rhodes, C. and Berg, P. (1977). J. Mol. Biol. 113, 237–251.
17. Grunstein, M. and Hogness, D. S. (1975). Proc. Nat. Acad. Sci., U.S.A. 72, 3961–3965.
18. Taylor, J. M. Illemensee. R. and Summers. J. (1976). Biochim. Biophys. Acta 442, 324–330.
19. Messing, J., Crea, R. and Seeberg, P. H. (1981). Nucleic Acids Res. 9, 309–321.
20. Sanger, F., Nicklen, S. and Coulson, A. R. (1977). Proc. Natl. Acad. Sci. U.S.A. 74, 5463–5467.
21. Smith, A. J. H. (1979). Nucleic Acids Res. 6, 831–848.
22. Herring, A. J., Inglis, N. F., Ojeh, C. K., Snodgrass, D. R. and Menzies, J. D. (1982). J. Clin. Microbiol. 16, 473–477.
23. Laemmli, U. K. (1970). Nature 227, 680–685.
24. Holmes, I. H. (1983). In "Reoviridae" (ed. W. K. Joklik) pp. 365–367 (Plenum, N.Y.).
25. Wyatt, R. G., James, W. D., Bohl, E. H., Theil, K. W., Saif, L. J., Kalica, A. R., Greenberg, H. B., Kapikian, A. Z. and Chanock, R. M. (1980). Science 207, 189–191.
26. Woode, G. N., Bridger, J. C., Hall, G. and Dennis, M. J. (1974). Res. Vet. Sci. 16, 102–105.
27. Rodger, S. M., Bishop, R. F., Birch, C., McLean, B. and Holmes, I. H. (1981). J. Clin. Microbiol. 13, 272–278.
28. Kalica, A. R., Greenberg, H. B., Espejo, R. T., Flores, J., Wyatt, R. G., Kapikian, A. Z. and Chanock, R. M. (1981). Infect. Immun. 33, 958–961.
29. Beards, G. M. (1982). Archiv. Virol. 74, 65–70.
30. Thouless M. E., Beards, G. M. and Flewett, T. H. (1982). Arch. Virol. 73, 219–230.
31. Urasawa, S. Urasawa. T. and Taniguchi, K. (1982). Infect. Immun. 38, 781–784.
32. Rodger. S. M., Schnagl, R. D. and Holmes, I. H. (1977). J. Virol. 24, 91–98.
33. Wyatt, R. G., Greenberg, H. B., James, W. D., Pittman, A. L. Kalica, A. R., Flores, J., Chanock, R. M. and Kapikian, A. Z. (1982). Infect. Immun. 37, 110–115.
34. Clarke, I. N. and McCrae, M. A. (1983). J. Gen. Virol. 64, 1877–1884.
35. Imai, M., Akatani, K., Ikegami, N. and Furuichi, Y. (1983). J. Virol. 47, 125–136.
36. Ericson, B. L., Graham, D. Y. Mason, B. B. and Estes, M. K. (1982). J. Virol. 42, 825–839.
37. Arias. C. F., Lopez, S. and Espejo, R. T. (1982). J. Virol. 41, 42–50.
38. McCrae, M. A. and Faulkner-Valle, G. P. (1981). J. Virol. 39, 490–496.
39. Kreil, G. (1981). Annu. Rev. Biochem. 50, 317–348.
40. Perlman, D. and Halvorson, H. O. (1983). J. Mol. Biol. 167, 391–409.
41. Ericson, B. L., Graham, D. Y., Mason, B. B Hanssen, H. H. and Estes, M. K. (1983). Virology 127, 320–332.
42. Sonza, S., Breschkin, A. M. and Holmes, I. H. (1984). Virology 134, 318–327.

43. Kapikian, A. Z., Cline, W. L., Kim, H. W., Kalica, A. R., Wyatt, R. G. van Kirk, D. H., Channock, R. M., James, H. D., Jr. and Vaughn, A. L. (1976). Proc. Soc. Exp. Biol. Med. 152, 535–539.
44. Woode, G. N., Bridger, J. C., Jones, J. M., Flewett, T. H., Bryden, A. S., Davies, H. A. and White, G. B. B. (1976). Infect. Immunol. 14, 804–810.
45. Thouless, M. E., Bryden, A. S., Flewett, T. H. Woode, G. N., Bridger, J. C., Snodgrass, D. R. and Herring, J. A. (1977). Arch. Virol. 53, 287–294.
46. Joklik, W. K. (1983). In "The Reoviridae" (ed. W. K. Joklik) pp. 1–7 (Plenum, N.Y., (1983).
47. Gaillard, R. K. and Joklik, W. K. (1982). Virology 123, 152–164.
48. Malherbe, H. H. and Stricland-Cholmley, M. (1967). Arch. Gesamte Virusforsch. 22, 235–245.
49. Stuker, G., Oshiro, L. S. and Schmidt, N. J. (1980). J. Clin. Microbiol. 11, 202–203.
50. Both, G. W., Sleigh, M. J., Cox, N. J. and Kendal, A. P. (1983). J. Virol. 48, 52–60.
51. S. B. Formal, L. S. Baron, D. J. Kopecko, 0. Washington, C. Powell and C. A. Life (1981). Construction of a potential bivalent vaccine strain=introduction of *Shigella sonnei* form 1 antigen genes into the gal *E Salmonella typhi* Ty 21a typhoid vaccine strain. Infect. Immun. 34, 746–750.
52. T. J. Silhavy, H. Shumn, J. Beckwith and M. Schwartz (1977). Use of gene fusions to study outer membrane protein localization in *Escherichia coli.* Proc. Natl. Acad. Sci. USA 74, 5411–5415.
53. T. M. Roberts, I. Birel, R. R. Yocum, D. M. Livingston and M. Ptashne (1979) Synthesis of simian virus 40 antigen in *Escherichia coli.* Proc. Natl. Acad. Sci. USA 76, 5596–5600.

The claims form part of the disclosure of this specification.

Modifications and adaptations may be made to the above described without departing from the spirit and scope of this invention which includes every novel feature and combination of features disclosed herein.

We claim:

1. An isolated nucleic acid encoding the major outer capsid glycoprotein of human serotype 2 rotavirus wherein said nucleic acid comprises the nucleotide sequence:

```
5'-GGCTTTAAAAACGAGAATTTCCGT
                    CTGGCTAGCGGTTAGCTCTTTTTA⁴⁸
ATG  TAT  GGT  ATT  GAA  TAT  ACC
     ACA  ATT  CTG  ACC  ATT  TTG⁸⁷
ATA  TCT  ATC  ATA  TTA  TTG  AAT
     TAT  ATA  TTA  AAA  ACT¹²³
ATA  ACT  AAT  ACG  ATG  GAC  TAC
     ATA  ATT  TTC  AGG  TTT  TTA¹⁶²
CTA  CTC  ATT  GCT  TTA  ATA  TCA
     CCA  TTT  GTA  AGG  ACA¹⁹⁸
CAA  AAT  TAT  GGC  ATG  TAT  TTA
     CCA  ATA  ACG  GGA  TCA  CTA²³⁷
GAC  GCT  GTA  TAT  ACG  AAT  TCT
     ACT  AGT  GGA  GAG  CCA²⁷³
TTT  TTA  ACT  TCG  ACG  CTG  TGT
     TTA  TAC  TAT  CCA  GCA  GAA³¹²
GCT  AAA  AAT  GAG  ATT  TCA  GAT
     GAT  GAA  TGG  GAA  AAT³⁴⁸
ACT  TTA  TCA  CAA  TTA  TTT  TTA
     ACT  AAA  GGA  TGG  CCA  ATT³⁸⁷
GGA  TCA  GTT  TAT  TTT  AAA  GAC
     TAC  AAT  GAT  ATT  AAT⁴²³
ACA  TTT  TCT  GTG  AAT  CCA  CAA
     CTA  TAT  TGT  GAT  TAT  AAT⁴⁶²
GTA  GTA  TTG  ATG  AGA  TAT  GAC
     AAT  ACA  TCT  GAA  TTA⁴⁹⁸
GAT  GCA  TCA  GAG  TTA  GCA  GAT
     CTT  ATA  TTG  AAT  GAA  TGG⁵³⁷
CTG  TGC  AAT  CCT  ATG  GAT  ATA
     TCG  CTT  TAC  TAT  TAT⁵⁷³
CAA  CAA  AGT  AGC  GAA  TCA  AAT
     AAA  TGG  ATA  TCG  ATG  GGA⁶¹²
ACA  GAC  TGC  ACG  GTA  AAA  GTT
     TGT  CCA  CTC  AAT  ACA⁶⁴⁸
CAA  ACC  CTA  GGG  ATT  GGA  TGC
     AAA  ACT  ACG  GAT  GTA  AAC⁶⁸⁷
ACA  TTT  GAG  ATT  GTT  GCG  TCG
     TCT  GAA  AAA  TTA  GTA⁷²³
ATT  ACT  GAC  GTT  CTA  AAT  GGT
     GTT  AAC  CAT  AAC  ATA  AAT⁷⁶²
ATT  TCA  ATA  AAT  ACG  TGC  ACT
     ATA  CGC  AAC  TGT  AAT⁷⁹⁸
AAA  TTA  GGA  CCA  CGA  GAA  AAT
     GTT  GCT  ATA  ATT  GAA  GTT⁸³⁷
GGT  GGA  CCG  AAC  GCA  TTA  GAT
     ATC  ACT  GCT  GAT  CCA⁸⁷³
ACA  ACA  GTC  CCA  CAA  GTT  CAA
     AGA  ATC  ATG  CGA  ATA  AAT⁹¹²
TGG  AAA  AAA  TGG  TGG  CAA  GTA
     TTT  TAT  ACA  GTA  GTT⁹⁴⁸
GAC  TAT  ATT  AAC  CAA  GTT  ATA
     CAA  GTC  ATG  TCC  AAA  CGA⁹⁸⁷
TCA  AGA  TCA  TTA  GAC  GCA  GGT
     GCT  TTT  TAT  TAT  AGA¹⁰²³
```

-continued

| | |
|---|---|
| ATT | TAG |
| ATATAGATTTGGTCAGATTTGTATGATGTGACC-3′1062. | |

2. A vector comprising the isolated nucleic acid of claim 1.

3. A host cell comprising the vector of claim 2.

4. An isolated major outer capsid glycoprotein of which comprises the amino acid sequence:

| | | | | | | | | | | | | |
|---|---|---|---|---|---|---|---|---|---|---|---|---|
| Met | Tyr | Gly | Ile | Glu | Tyr | Thr | Thr | Ile | Leu | Thr | Ile | Leu$_{13}$ |
| Ile | Ser | Ile | Ile | Leu | Leu | Asn | Tyr | Ile | Leu | Lys | Thr$_{25}$ | |
| Ile | Thr | Asn | Thr | Met | Asp | Tyr | Ile | Ile | Phe | Arg | Phe | Leu$_{38}$ |
| Leu | Leu | Ile | Ala | Leu | Ile | Ser | Pro | Phe | Val | Arg | Thr$_{50}$ | |
| Gln | Asn | Tyr | Gly | Met | Tyr | Leu | Pro | Ile | Thr | Gly | Ser | Leu$_{63}$ |
| Asp | Ala | Val | Tyr | Thr | Asn | Ser | Thr | Ser | Gly | Glu | Pro$_{75}$ | |
| Phe | Leu | Thr | Ser | Thr | Leu | Cys | Leu | Tyr | Tyr | Pro | Ala | Glu$_{88}$ |
| Ala | Lys | Asn | Glu | Ile | Ser | Asp | Asp | Glu | Trp | Glu | Asn$_{100}$ | |
| Thr | Leu | Ser | Gln | Leu | Phe | Leu | Thr | Lys | Gly | Trp | Pro | Ile$_{113}$ |
| Gly | Ser | Val | Tyr | Phe | Lys | Asp | Tyr | Asn | Asp | Ile | Asn$_{125}$ | |
| Thr | Phe | Ser | Val | Asn | Pro | Gln | Leu | Tyr | Cys | Asp | Tyr | Asn$_{138}$ |
| Val | Val | Leu | Met | Arg | Tyr | Asp | Asn | Thr | Ser | Glu | Leu$_{150}$ | |
| Asp | Ala | Ser | Glu | Leu | Ala | Asp | Leu | Ile | Leu | Asn | Glu | Trp$_{162}$ |
| Leu | Cys | Asn | Pro | Met | Asp | Ile | Ser | Leu | Tyr | Tyr | Tyr$_{175}$ | |
| Gln | Gln | Ser | Ser | Glu | Ser | Asn | Lys | Trp | Ile | Ser | Met | Gly$_{188}$ |
| Thr | Asp | Cys | Thr | Val | Lys | Val | Cys | Pro | Leu | Asn | Thr$_{200}$ | |
| Gln | Thr | Leu | Gly | Ile | Gly | Cys | Lys | Thr | Thr | Asp | Val | Asn$_{213}$ |
| Thr | Phe | Glu | Ile | Val | Ala | Ser | Ser | Glu | Lys | Leu | Val$_{225}$ | |
| Ile | Thr | Asp | Val | Val | Asn | Gly | Val | Asn | His | Asn | Ile | Asn$_{238}$ |
| Ile | Ser | Ile | Asn | Thr | Cys | Thr | Ile | Arg | Asn | Cys | Asn$_{250}$ | |
| Lys | Leu | Gly | Pro | Arg | Glu | Asn | Val | Ala | Ile | Ile | Gln | Val$_{263}$ |
| Gly | Gly | Pro | Asn | Ala | Leu | Asp | Ile | Thr | Ala | Asp | Pro$_{275}$ | |
| Thr | Thr | Val | Pro | Gln | Val | Gln | Arg | Ile | Met | Arg | Ile | Asn$_{288}$ |
| Trp | Lys | Lys | Trp | Trp | Gln | Val | Phe | Tyr | Thr | Val | Val$_{300}$ | |
| Asp | Tyr | Ile | Asn | Gln | Val | Ile | Gln | Val | Met | Ser | Lys | Arg$_{313}$ |
| Ser | Arg | Ser | Leu | Asp | Ala | Ala | Ala | Phe | Tyr | Tyr | Arg$_{325}$ | |
| Ile$_{326}$. | | | | | | | | | | | | |

* * * * *